United States Patent [19]

Rozsa et al.

[11] Patent Number: 5,783,573
[45] Date of Patent: Jul. 21, 1998

[54] PHARMACEUTICALS WHICH PROMOTE GASTROINTESTINAL BLOOD CIRCULATION

[75] Inventors: Susanna Rozsa; Julius Gy. Papp, both of Szeged, Hungary; Dirk Thormaehlen, Rheden; Harald Waldeck, Isernhagen, both of Germany

[73] Assignee: Solvay Pharmaceuticals GmbH, Hanover, Germany

[21] Appl. No.: 929,114

[22] Filed: Sep. 15, 1997

[30] Foreign Application Priority Data

Sep. 18, 1996 [DE] Germany .................. 196 38 020.0

[51] Int. Cl.$^6$ .................................................. A61K 31/55
[52] U.S. Cl. ........................................ 514/213; 514/211
[58] Field of Search ................................ 514/213, 211

[56] References Cited

U.S. PATENT DOCUMENTS 5,677,297  10/1997  Waldeck et al. ................. 514/211

*Primary Examiner*—William R. A. Jarvis
*Attorney, Agent, or Firm*—Evenson, McKeown, Edwards & Lenahan P.L.L.C.

[57] ABSTRACT

The use is described of compounds of the general formula I

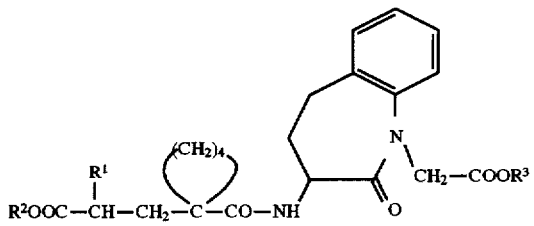

wherein $R^1$ represents a phenyl-lower alkyl group which can optionally be substituted in the phenyl ring by lower alkyl, lower alkoxy or halogen, or represents a naphthyl-lower alkyl group, $R^2$ denotes hydrogen or a biolabile ester-forming group, and $R^3$ denotes hydrogen or a biolabile ester-forming group, and physiologically acceptable salts of the acids of formula I for preparing pharmaceutical compositions for the treatment and/or prophylaxis of gastrointestinal blood circulation disturbances.

6 Claims, No Drawings

PHARMACEUTICALS WHICH PROMOTE GASTROINTESTINAL BLOOD CIRCULATION

BACKGROUND OF THE INVENTION

The present invention relates to the use of benzazepine-N-acetic acid derivatives which contain an oxo group in the α position relative to the nitrogen atom and are substituted in the 3 position by a 1-(carboxyalkyl) cyclopentylcarbonylamino radical, and their salts and biolabile esters for the treatment and/or prophylaxis of blood circulation disturbances in the gastrointestinal region and for the preparation of pharmaceuticals which are suitable for this treatment.

SUMMARY OF THE INVENTION

The underlying object of the invention is to develop novel pharmaceutical compositions for improving blood circulation in the gastrointestinal region and for the treatment and/or prophylaxis of symptoms which arise in connection with blood circulation disturbances in the gastrointestinal region.

According to the invention, compounds of the general formula I

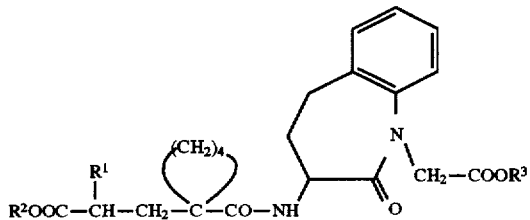

in which
$R^1$ represents a phenyl-lower alkyl group which can optionally be substituted in the phenyl ring by lower alkyl, lower alkoxy or halogen, or represents a naphthyl-lower alkyl group,
$R^2$ denotes hydrogen or a biolabile ester-forming group, and
$R^3$ denotes hydrogen or a biolabile ester-forming group, and physiologically tolerated salts of the acids of the formula I are used for preparing pharmaceutical compositions for the treatment and/or prophylaxis of blood circulation disturbances in the gastrointestinal region.

If the substituents denote or contain lower alkyl groups or alkoxy groups in the compounds of the formula I, these groups can be straight-chain or branched and contain, in particular, from 1 to 4, preferably from 1 to 2, carbon atoms and preferably represent methyl or methoxy. If the substituents contain halogen, those halogens which are preferred are, in particular, fluorine, chlorine or bromine, particularly preferably fluorine or chlorine.

In the radial $R^1$, the lower alkylene chain can contain from 1 to 4, preferably from 1 to 2, carbon atoms. In particular, $R^1$ represents an optionally substituted phenethyl group which can be optionally substituted once or more than once by halogen, lower alkoxy or lower alkyl, or represents a naphthylethyl group.

The compounds of the formula I constitute optionally esterified dicarboxylic acid derivatives. Depending on the mode of administration, biolabile monoesters, in particular compounds in which $R^2$ denotes a biolabile ester-forming group and $R^3$ denotes hydrogen, or di-carboxylic acids are preferred, with the latter being particularly suitable for i.v. administration.

Suitable biolabile ester-forming groups $R^2$ and $R^3$ are lower alkyl groups, phenyl or phenyl-lower alkyl groups which are optionally substituted in the phenyl ring by lower alkyl or by a lower alkylene chain which is bonded to two adjacent carbon atoms, dioxolanylmethyl groups which are optionally substituted in the dixolane ring by lower alkyl, or $C_2$-$C_6$-alkanoyloxymethyl groups which are optionally substituted on the oxymethyl group by lower alkyl. If the biolabile ester-forming group $R^2$ or $R^3$ denotes lower alkyl, the latter can represent a preferably unbranched alkyl group having from 1 to 4, preferably 2, carbon atoms. If the biolabile ester-forming group represents an optionally substituted phenyl-lower alkyl group, the alkylene chain of the latter can contain from 1 to 3, preferably 1, carbon atoms. If the phenyl ring is substituted by a lower alkylene chain, the latter can contain from 3 to 4, in particular 3, carbon atoms. Suitable phenyl-containing substituents $R^2$ and/or $R^3$ are, in particular, phenyl, benzyl or indanyl. If $R^2$ and/or $R^3$ represent an optionally substituted alkanoyloxymethyl group, their alkanoyloxy group can contain from 2 to 6, preferably from 3 to 5, carbon atoms and is preferably branched and can, for example, represent a pivaloyloxymethyl radical (=tert-butylcarbonyloxymethyl radical).

Suitable physiologically acceptable salts of dicarboxylic acids or monoesters of the formula I are their alkali metal, alkaline earth metal or ammonium salts, for example sodium or potassium salts, or salts with physiologically acceptable, pharmacologically neutral organic amines, such as diethylamine or tert-butylamine.

The compounds of the formula I contain two asymmetric or chiral carbon atoms, namely the carbon atom which carries the amide side chain and which is in the 3 position of the ring skeleton and the carbon atom of the amide side chain which carries the radical $R^1$. Consequently, the compounds can exist in several optically active stereoisomeric forms or as racemates. Both the racemic mixtures and the isomerically pure compounds of the formula I can be used in accordance with the present invention.

The compounds which are employed in accordance with the invention for treating blood circulation disturbances in the gastrointestinal region come within the scope of benzazepine-, benzoxazepine- and benzothiazepine-N-acetic acid derivatives which are described in German patent application No. 195 10 566.4, which contain an oxo group in the α position relative to the nitrogen and are substituted in the 3 position by a 1-(carboxyalkyl) cyclopentylcarbonylamino radical, and which exert NEP-inhibitory effects on the heart.

It has now been found, surprisingly, that the group of compounds of the formula I which is used in accordance with the invention promotes blood circulation in the mesenteric vascular system in humans and larger mammals and is suitable for the treatment and/or prophyl-axis of gastrointestinal disorders which are associated with reduced gastrointestinal blood circulation due to a wide range of causes, in particular for the treatment and/or prophylaxis of abdominal angina. There can be many different reasons for a reduced gastrointestinal blood circulation, e.g. an increased vascular resistance, for example in the case of vascular changes due to arteriosclerosis or inflammations of the blood vessels which supply the gastrointestinal region, or pathological changes in vascular function which can be connected to diabetes and/or cardiac diseases such as hypertensive cardiomyopathy.

Diminished blood flow in the mesenteric artery results in a blood supply in the gastrointestinal wall which is insufficient to ensure the blood circulation which is required for satisfactorily operating gastrointestinal motility and, in particular, is no longer adequate to meet the increased requirement for motility, secretion and absorption following food intake. Inadequate blood supply to the intestinal walls can manifest itself in gastrointestinal symptoms which range from acute or chronic pains in the abdominal region through to acute attacks of abdominal angina, which attacks can occur particularly violently following food intake, and also flatulence, constipation or diarrhoea.

The effect of the compounds of the formula I which are used in accordance with the invention in promoting blood circulation in the mesenteric vascular system was demonstrated in in-vivo pharmacological tests on healthy rats and diabetic rats by measuring the effect of the substances on blood flow in the mesenteric artery.

DESCRIPTION OF THE TEST METHOD

The tests were carried out on adult male Wistar rats having an initial body weight of 250–270 g. The animals were divided into 4 groups of 10 animals each. In two of the groups, diabetes was induced in the animals by a single i.p. injection of streptozotocin (dose, 65 mg/kg).

During the subsequent 8-week test period, all the animals had unlimited access to drinking water and received a standard rodent feed.

One group of healthy rats and one group of diabetic rats were given a daily oral dose of the test substance (30 mg/kg of body weight) together with the feed.

After 8 weeks had passed, the animals were anaesthetized by the i.p. injection of pentobarbital (45 mg/kg of body weight) and tracheotomized; following laparotomy in the midline, the main stem of the mesenteric artery was exposed in order to attach a blood flow measurement probe to the vessel. A calibrated sensor was used to determine intestinal blood flow in the resting state by means of an ultrasonic method for measuring changes in blood flow time (ultrasonic transit time shift technique), which method measures blood flow volume in ml/minute.

In this test method, treatment with the substance from Example 6 below led, both in the healthy rats and in the diabetic rats, to a significant increase in mesenteric blood flow as compared with the respective control groups which were not treated with the test substance, as is evident from Table A below.

TABLE A

| Animal group | Intestinal blood flow in ml/min |
|---|---|
| Healthy rats untreated control group of animals | 12 |
| Healthy rats group treated with the test substance | 15 |
| Diabetic rats control group of animals which is not treated with the test substance | 9 |
| Diabetic rats group treated with the test substance | 14 |

Due to their above-described effect, the compounds of the formula I are suitable, as pharmaceuticals for larger mammals, in particular humans, for the treatment and/or prophylaxis of blood circulation disturbances in the gastrointestinal region and of disease states which are due to such disturbances, in particular abdominal angina. For this, dicarboxylic acids of the formula I, and their salts, are advantageously employed in medicinal forms which can be administered parenterally, in particular i.v., and monoesters or diesters of the formula I are advantageously employed in medicinal forms which can be administered orally. The doses to be used can differ between individuals and naturally vary depending on the nature of the condition to be treated, on the substance used and on the mode of administration. For example, parenteral formulations will generally comprise less active compound than will oral preparations. In general, however, medicinal forms having an active compound content of from 1 to 200 mg per single dose are suitable for administration to larger mammals, in particular humans.

As drugs, the compounds of the formula I can be included, together with customary pharmaceutical auxiliary substances, in pharmaceutical compositions such as tablets, capsules, suppositories or solutions. These pharmaceutical compositions can be prepared by methods which are known per se using customary solid or liquid carrier substances such as lactose, starch or talc or liquid paraffins, and/or using customary pharmaceutical auxiliary substances, for example tablet disintegrants, solubilizing agents or preservatives.

The compounds of formula I which are used in accordance with the invention can be prepared by the methods which are described in the abovementioned German patent application No. 195 10 566.4.

For example, the compounds of the formula I which are used in accordance with the invention, and their salts, can be obtained, in a manner known per se, by reacting acids of the general formula II

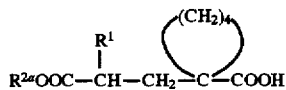

in which $R^1$ has the above meaning and $R^{2a}$ is an acid protecting group, or their reactive acid derivatives, with amines of the general formula III

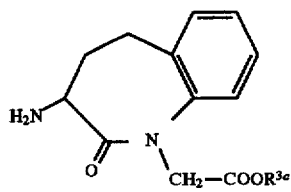

in which $R^{3a}$ denotes an acid protecting group, to give amides of the general formula IV

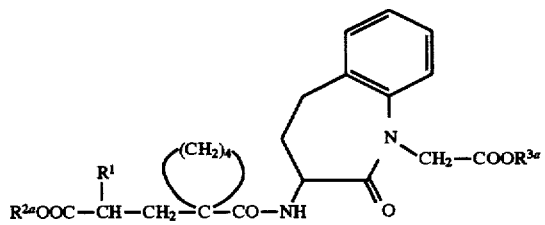

in which $R^1$, $R^{2a}$ and $R^{3a}$ have the above meaning, and, in the compounds of formula IV, eliminating, simultaneously or consecutively in any order, the acid protecting groups $R^{2a}$ and $R^3$, provided these do not represent a desired biolabile ester-forming group, and, if desired, esterifying the acid group which in each case becomes free with an alcohol of the general formula V

$R^4$—OH or a corresponding reactive derivative of the general formula Va

$R^4$—X in which $R^4$ represents a biolabile ester-forming group and X denotes a reactive group which can be eliminated, and, if desired, converting resulting acids of the formula I into their physiologically tolerated salts or converting salts of the acids of the formula I into the free acids.

The reaction of the acids of the formula II with the amines of the formula III to give the amides of the formula IV can be carried out using methods which are customary per se for forming amide groups by means of aminoacylation. The acids of the formula II, or their reactive derivatives, can be employed as acylating agents. Mixed acid anhydrides and acid halides are particularly suitable reactive derivatives. Thus, for example, acid chlorides or acid bromides of the acids of the formula II, or mixed esters of the acids of the formula II with organic sulfonic acids, for example lower alkanesulfonic acids, such as methanesulfonic acid, or aromatic sulfonic acids, such as benzenesulfonic acid, or lower alkyl-substituted or halogen-substituted benzenesulfonic acids, for example toluenesulfonic acids or bromobenzenesulfonic acids, can be employed. The acylation can take place in an organic solvent which is inert under the reaction conditions, preferably at temperatures of between −20° C. and room temperature. Suitable solvents are, in particular, halogenated hydrocarbons, such as dichloromethane, or aromatic hydrocarbons, such as benzene or toluene, or cyclic ethers, such as tetrahydrofuran or dioxane, or mixtures of these solvents.

Particularly when a mixed anhydride of the acids of the formula II with a sulfonic acid is used as the acylating agent, the acylation can expediently be carried out in the presence of an acid-binding reagent. Suitable acid-binding agents are bases which are soluble in the reaction mixture, in particular organic bases such as tert-lower alkylamines and pyridines, such as triethylamine, tripropylamine, pyridine, 4-dimethylaminopyridine, 4-diethylaminopyridine or 4-pyrrolidinopyridine. Organic bases which are employed in excess may also be used at the same time as solvents.

Advantageously, mixed acid anhydrides of the acids of the formula II with organic sulfonic acids can be obtained in situ by reacting the acids of the formula II with an acid halide, in particular the acid chloride, of the organic sulfonic acid, and directly subjected, without isolation, to further reaction with the amine compound of the formula III.

If the acids of the formula II are themselves employed as acylating agents, the reaction of the amino compounds of the formula III with the acids of the formula II can expediently also be carried out in the presence of a coupling reagent which is known from peptide chemistry to be suitable for amide formation. Examples of coupling reagents which promote amide formation with the free acids by reacting with the acid in situ with the formation of a reactive acid derivative and which may particularly be mentioned are alkylcarbodiimides, for example cycloalkylcarbodiimide such as dicyclohexylcarbodiimide or 1-ethyl-3-[3-(dimethylamino)propyl]carbodiimide, carbonyldiimidazole and N-lower alkyl-2-halopyridinium salts, in particular halides or tosylates, preferably N-methyl-2-chloropyridinium iodide (see, for example, Mukaijama in Angewandte Chemie 91, pages 789–812). The reaction in the presence of a coupling reagent can expediently be carried out at temperatures of from −30° to +50° C. using solvents such as halogenated hydrocarbons and/or aromatic solvents, where appropriate in the presence of an acid-binding amine.

Provided they do not represent biolabile ester-forming groups in the compounds of the formula I, the protecting groups $R^{2a}$ and $R^{3a}$ can be eliminated in a manner known per se from the compounds of the formula IV which are obtained by reacting the compounds of the formula II with the compounds of the formula III.

Protecting groups which are customary per se for protecting acid functions, and which are subsequently eliminated once again by methods which are known per se, can be selected as protecting groups $R^{2a}$ and $R^{3a}$. Suitable acid-protecting groups are known, for example, from McOmie, "Protective Groups in Organic Chemistry", Plenum Press and Greene, "Protective Groups in Organic Synthesis" Wiley Interscience Publication.

If compounds of the formula I are to be prepared in which $R^2$ and $R^3$ are identical, it is expedient for identical protecting groups $R^{2a}$ and $R^{3a}$, to be selected in the starting compounds II and III.

If compounds of the formula I are to be prepared in which $R^2$ and $R^3$ have different meanings, it is expedient for different protecting groups to be selected in the starting compounds II and III, which protecting groups can be selectively eliminated once again under differing conditions in a manner known per se. The following may be mentioned as examples of three protecting groups which can be eliminated under differing conditions:

1. methyl or ethyl esters, which are readily cleaved under alkaline conditions but which are substantially more stable towards acid conditions or hydrogenolysis,
2. tert-butyl esters, which can readily be cleaved by acids but which are substantially more stable towards alkaline conditions or hydrogenolysis, and
3. benzyl esters, which can readily be cleaved hydrogenolytically or else under alkaline conditions, but which are substantially more stable towards acid conditions.

If, for example, dicarboxylic acid compounds of the formula I are to be prepared in which $R^2$ and $R^3$ are both hydrogen, protecting groups which can be eliminated under acid conditions, for example the tert-butyl group, are preferably employed as protecting groups $R^{2a}$ and $R^{3a}$, and the tert-butyl ester compounds of the formula IV which are obtained by reacting the compounds of the formula II with the compounds of the formula III are subsequently cleaved by treating with acid. The cleavage can be effected, for example, by treating with trifluoroacetic acid as such or with a trifluoroacetic acid solution in a halogenated hydrocarbon, for example dichloromethane, or by treating with HCl gas in an organic solvent which is inert under the reaction conditions, for example ethyl acetate. The reaction can be carried out at temperatures of between −25° C. and room temperature.

If, for example, monocarboxylic acid compounds of the formula I are to be prepared in which $R^2$ denotes a biolabile ester-forming group and $R^3$ is hydrogen, compounds in which $R^{2a}$ already represents the desired biolabile ester-forming group, e.g. the ethyl group, can be employed as starting compounds of the formula II, and protecting groups which are cleaved under conditions under which the $R^2$—OCO group is not cleaved can be employed as the protecting group $R^{3a}$ in the compounds of the formula III. If the $R^2$—OCO group is the ethyl ester group, which is relatively stable towards acid, the tert-butyl group, which can be eliminated by acid, or a group which can be eliminated hydrogenolytically, such as benzyl, are then suitable, for example, as the protecting group $R^{3a}$.

If $R^{2a}$ in the compounds of the formula II represents an acid-sensitive, biolabile ester-forming group, a group which can be eliminated hydrogenolytically, such as benzyl, is then expediently selected as protecting group $R^{3a}$ in the compounds of the formula III, and this protecting group is eliminated hydrogenolytically from the compounds of the formula IV which arise as a result of the reaction of the compounds of the formula II with the compounds of the formula III. The hydrogenolysis can be effected by catalytic hydrogenation in the presence of a catalyst, preferably a Pd/C catalyst, in an organic solvent which is inert under the reaction conditions, for example a lower alcohol, such as ethanol, or a lower alkyl ester, such as ethyl acetate. Expediently, the catalytical hydrogenation is carried out at room temperature and under a hydrogen pressure of from 4 to 5 bar.

However, in order to prepare compounds of the formula I in which $R^2$ denotes a biolabile ester-forming group and $R^3$ denotes hydrogen, starting compounds of the formulae II and III can also be selected which possess differing protecting groups $R^{2a}$ and $R^3$a having differing reactivities, and the protecting group $R^{2a}$ can initially be eliminated, while retaining the protecting group $R^3$, from the compounds of the formula IV which result from reaction of the compounds of the formula II with the compounds of the formula III, and the desired biolabile ester-forming group $R^2$ can then be inserted in the reaction product of the general formula IV'

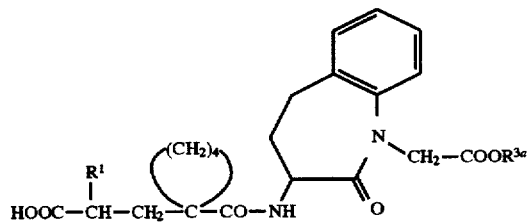

in which $R^1$ and $R^{3a}$ have the above meanings, by reacting the free acid group of the compound of the formula IV' with a compound of the formula V or Va, and the protecting group $R^{3a}$ can subsequently be eliminated from the resulting compounds of the formula IV.

Thus, for example, it can initially only be the protecting group $R^{2a}$ which is eliminated under acid conditions from compounds of formula IV in which $R^{2a}$ denotes a protecting group which can be eliminated by acid, in particular the tert-butyl group, and $R^3$a denotes an acid-stable protecting group, e.g. benzyl. The resulting monocarboxylic acid of the formula IV' can then be esterified with an alcohol of the formula V or a corresponding compound of the formula Va using methods which are customary per se for ester formation. Suitable eliminable reactive groups X in the compounds of the formula Va are halogens, in particular chlorine or bromine, or an organic sulfonic acid radical, for example the radical of a lower alkanesulfonic acid, such as methanesulfonic acid, or of aromatic sulfonic acids, such as benzenesulfonic acid, or benzenesulfonic acids which are substituted by lower alkyl or halogen, such as toluenesulfonic acids. For the esterification, alcohols of the formula V can, for example, be reacted with an acid of the formula IV', or a reactive acid derivative of this acid, in a manner which is known per se for acylating alcohols. The reaction can be carried out, for example, under the reaction conditions given for reacting compounds of the formula II with compounds of the formula III.

In an analogous manner, compounds of the formula I in which $R^3$ denotes a biolabile ester-forming group and $R^2$ denotes hydrogen or a biolabile ester-forming group which is different from $R^3$ can also be prepared by selecting appropriate differing protecting groups.

In the above-described reactions, the asymmetric centers in the starting compounds of formulas II and III are not altered so that, depending on the nature of the starting compounds, isomerically pure compounds of the formula I, or isomeric mixtures, can be obtained. In order to prepare isomerically pure, and consequently optically uniform, compounds of the formula I, enantiomerically pure compounds of the formula II are expediently reacted with enantiomerically pure compounds of the formula III. If an enantiomerically pure compound of the formula II is reacted with a racemic compound of the formula III, or a racemic compound of the formula II is reacted with an enantiomerically pure compound of the formula III, a mixture of two diastereomers is in each case obtained, which mixture can, if desired, be resolved in a manner which is known per se. The reaction of racemic compounds of the formula II with racemic compounds of the formula III yields corresponding mixtures of 4 isomers, which mixtures can, if desired, be resolved in a manner known per se.

The starting compounds of the formula II can be obtained by methods which are known per se, for example by reacting acrylic acid derivatives of the general formula VI

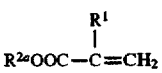

in which $R^{2a}$ and $R^1$ have the above meanings, with cyclopentanecarboxylic acid of the formula VII

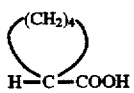

The reaction can be effected in a known manner under the conditions of a Michael addition in an organic solvent which is inert under the reaction conditions, by reacting the cyclopentanecarboxylic acid with a strong base which is capable of forming the dianion of the cyclopentanecarboxylic acid and subsequently reacting with the acrylic ester derivative of the formula VI. Suitable solvents are ethers, in particular cyclic ethers, such as tetrahydrofuran. Suitable strong bases are non-nucleophilic, organic alkali metal amides, such as lithium diisopropylamide. Advantageously, the cyclopentanecarboxylic acid is reacted, in tetrahydrofuran, with two equivalents of lithium diisopropylamide and the reaction mixture is then subjected to further reaction with the compound of the formula VI. The reaction temperature can be between −70° and 0° C.

The compounds of the formula II possess an asymmetric center at the carbon atom carrying the radical $R^1$ and are obtained during the synthesis in the form of their racemates. The optically active compounds can be obtained from the racemic mixtures in a known manner, for example by chromatographic separation on chiral separating materials or by reaction with suitable optically active bases, e.g. α-methylbenzylamine or pseudoephedrine followed by resolution into their optical antipodes by fractional crystallization of the isolated salts.

Acrylic ester derivatives of the formula VI can be obtained, in a manner known per se, by reacting (di-lower talkylphosphono)acetic ester derivatives of the general formula VIII

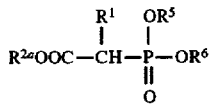

in which $R^{2a}$ and $R^1$ have the above meanings and $R^5$ and $R^6$ in each case denote lower alkyl, preferably methyl or ethyl, with formaldehyde under alkaline conditions and in an organic solvent which is inert under the reaction conditions. For example, compounds of the formula VIII can be reacted with paraformaldehyde in an ether, preferably a cyclic ether, such as tetrahydrofuran, in the presence of a base, preferably a non-nucleophilic alkali metal alcoholate such as potassium tert-butoxide, at temperatures of between −20° and +30° C.

Compounds of formula VIII can be obtained in a known manner by reacting phosphonoacetic acid derivatives of the general formula IX

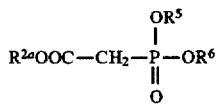

in which $R^{2a}$, $R^5$ and $R^6$ have the above meanings, with compounds of the formula X

in which $R^1$ and X have the above meanings. The reaction can be carried out under conditions which are customary for alkylation, in a polar, aprotic organic solvent which is inert under the reaction conditions, in the presence of a base and at temperatures of between 0° and 80° C. Preferably, compounds of the formula X are employed in which X denotes halogen, in particular bromine or iodine, or tosylate. Examples of suitable solvents are amides, such as dimethylformamide, or else ethers. Suitable bases are non-nucleophilic alkali metal alcoholates, such as potassium tert-butoxide.

Compounds of the formula VI can also be obtained by treating malonic acid derivatives of the general formula XI

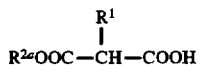

in which $R^{2a}$ and $R^1$ have the above meanings, in a known manner with formaldehyde under alkaline conditions. Thus, malonic acid derivatives of the formula XI can, for example, be reacted with aqueous formaldehyde solution in the presence of a secondary organic amine, in particular piperidine, at temperatures of between 0° and 30° C., preferably at temperatures which are below room temperature. The malonic acid derivatives of the formula XI can also be reacted with paraformaldehyde in pyridine at temperatures at from 40° to 60° C.

The malonic monoesters of the formula XI can be obtained by reacting malonic diesters of the general formula XII

in which $R^{2a}$ has the above meaning and $R^7$ denotes lower alkyl, in particular methyl, or benzyl, with compounds of the formula X and converting the resulting malonic diester derivatives of the general formula XIII

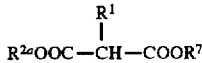

in which $R^1$, $R^{2a}$ and $R^7$ have the above meanings, by means of partial hydrolysis, into the corresponding malonic monoester derivatives of the formula XI.

The insertion of the radical $R^1$ into the malonic diesters of the formula XII can be effected in a known manner by reacting the esters of formula XII with a compound of formula X in a polar, aprotic organic solvent, preferably dimethylformamide, in the presence of a base, for example a non-nucleophilic alkali metal alcoholate, such as potassium tert-butoxide, at temperatures of between 0° C. and 8° C. The reaction can, for example, be carried out under the conditions given for the reaction of compounds of the formula VIII with compounds of the formula X.

The resulting substituted malonic diesters of the formula XIII can be converted into the corresponding malonic monoesters of the formula XI by eliminating the radical $R^7$ in a known manner. If the protecting group $R^{2a}$ and the radical $R^7$ represent different radicals having differing reactivities, those conditions under which the radical $R^{2a}$ is not attacked are advantageously selected for eliminating the radical $R^7$. If $R^7$ denotes benzyl, the elimination can be effected hydrogenolytically in a known manner. Lower alkyl esters $R^7$ are eliminated hydrolytically, under acid or alkaline conditions depending on the nature of the alkyl radical, in a manner known per se. Preferably, $R^7$ represents ethyl, which can be eliminated by alkaline hydrolysis. For this, the alkyl esters of the formula XIII can be treated, in a lower alcohol or a mixture of a lower alcohol and water, with an alkali metal hydroxide, for example potassium hydroxide. If the radicals $R^{2a}$ and $R^7$ are identical, the quantity of alkali metal hydroxide is then kept sufficiently low to ensure that only partial hydrolysis occurs.

Compounds of the formula III can be obtained in a known manner by reacting compounds of the general formula XIV

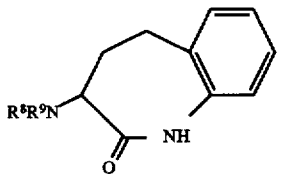

in which the $R^8R^9N$ group represents an amino group which is protected by an amino protecting group, with compounds of the general formula XV

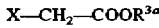

in which $R^3a$ and X have the above meanings, and liberating the free amino group from the $R^8R^9N$ group in the resulting reaction product of the general formula XVI

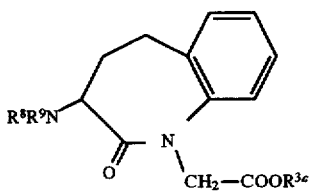

in which $R^{3a}$ and the $R^8R^9N$ group have the above meanings. The reaction of compounds of the formula XIV with compounds of the formula XV can be carried out using customary methods for alkylating amides. Preferably, compounds of the formula XV are employed in which X represents halogen, preferably bromine or iodine. The reaction can be carried out in a polar, aprotic organic solvent, for example dimethylformamide or a cyclic ether, such as tetrahydrofuran, in the presence of a base. Suitable bases are non-nucleophilic bases such as potassium tert-butoxide. If desired, the reaction can also be carried out in the presence of an alkali metal hydroxide, e.g. potassium hydroxide, in a two-phase system in the presence of a phase transfer catalyst, for example a tetra-lower alkylammonium halide, such as tetrabutylammonium bromide.

The amino group in the resulting compounds of the formula XVI can then be liberated by eliminating the protecting group in a known manner. The protecting groups which are known per se for protecting amino groups and which can be readily eliminated once again, for example the protecting groups which are known from peptide chemistry, can be employed for protecting the amino group. Suitable protecting groups are known, for example, from E. McOmie "Protective groups in organic chemistry" Plenum Press 1971. Examples of suitable protecting groups are the phthalimide group or the tert-butoxycarbonyl group or else the benzyloxycarbonyl group. Depending on the meaning of $R^{3a}$, it is in each case necessary to select protecting groups which can subsequently be eliminated under conditions under which the group $R^{3a}$ is not attacked.

The compounds of the formula III contain an asymmetric center at the carbon atom carrying the amino group. If optically pure starting compounds of the formula XIV are used as the starting material, optically pure compounds of the formula III are then obtained. If racemic compounds of the formula XIV are used as the starting material, compounds of the formula III which are also racemic are then obtained. Racemic mixtures of compounds of the formula III can be resolved into their optical isomers in a manner known per se, for example by chromatographic separation on chiral separating materials or by reaction with suitable optically active acids, for example tartaric acid, and subsequent resolution of the optical antipodes by fractional crystallization of the isolated salts. During the reaction with suitable optically active acids, and in order to increase the yield of the desired optical isomer, a reracemization of the isomer remaining in solution can be set in motion, in the reaction mixture, by adding a preferably aromatic aldehyde, such as benzaldehyde, at the same time as the salt of the one isomer with the optically active acid is largely precipitated or after this precipitation has taken place. In this case, the racemization at the asymmetric center is brought about by imine formation with the aldehyde.

The compounds of the formula XIV can be obtained in a known manner by replacing the halogen Y with the $R^8R^9N$ group, in a known manner in compounds of the general formula XVII

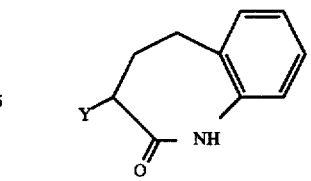

For example, a compound of the formula XVII can be reacted with an alkali metal salt of an amide $R^8R^9NH$, preferably potassium phthalimide. The reaction can take place in an aprotic organic solvent which is inert under the reaction conditions, preferably dimethylformamide, at temperatures of between 40° and 80° C.

Compounds of the formula XVII can be obtained, in a manner known per se, by means of a Beckmann rearrangement of oxime compounds of the general formula XVIII

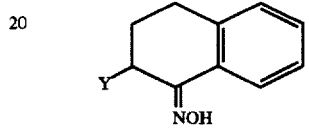

in which Y has the above meaning, by treating compounds of the formula XVIII with an acid under the conditions of a Beckmann rearrangement. Expediently, compounds of the formula XVIII are rearranged to give the compounds of the formula XVII by being treated with polyphosphoric acid at temperatures of between 60° and 90° C.

Oximes of the formula XVIII can be obtained from the cyclic ketone of the general formula XIX

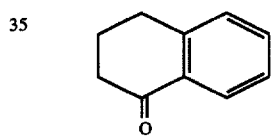

by initially treating the ketone of the formula XIX with halogen in order to introduce the radical Y and subsequently reacting the resulting halogenated ketones with hydroxylamine. Expediently, the α-halogenation of the ketone and the subsequent oxime formation can be carried out in a one-pot process, with the ketone of the formula XIX initially being treated with the halogen in an inert organic solvent, for example a lower alcohol such as methanol, and hydroxylamine subsequently being supplied to the reaction mixture. Expediently, the hydroxylamine is employed in the form of a hydroxylamine salt, for example the hydrochloride, and a little water is added to the reaction mixture. The procedure can be carried out at temperatures of between 0° and 40° C., preferably at room temperature.

While the following examples are intended to explain the invention in more detail, they do not restrict its scope in any way.

Examples 1 and 2 below describe pharmaceutical compositions according to the invention which comprise an active compound of the formula I and also the preparation of the pharmaceutical compositions.

EXAMPLE 1

Tablets which comprise (3S,2'R)-3-{1-[2'-(ethoxycarbonyl)-4,-phenylbutyl]cyclopentane-1-carbonylamino}-2,3,4,5-tetrahydro-2-oxo-1H-1-benzazepine-1-acetic acid.

Tablets were prepared having the following composition per tablet:

| | |
|---|---|
| (3S,2'R)-3-{1-[2'-(Ethoxycarbonyl)-4'-phenylbutyl]-cyclopentane-1-carbonylamio}-2,3,4,5-tetrahydro-2-oxo-1H-1-benzazepine-1-acetic acid | 20 mg |
| Corn starch | 60 mg |
| Lactose | 135 mg |
| Gelatin (as a 10% solution) | 6 mg |

The active compound, the corn starch and the lactose a were thickened with the 10% gelatin solution. The paste was comminuted and the resulting granulate was loaded on to a suitable metal plate and dried at 45° C. The dried granulate was passed through a crusher and mixed in a mixer with the following further auxiliary substances:

| | |
|---|---|
| Talc | 5 mg |
| Magnesium stearate | 5 mg |
| Corn starch | 9 mg |
| and then compressed into 240 mg tablets. | |

EXAMPLE 2

Injection solution which comprises (3S,2'R)-3-[1- (2'-carboxy-4'-phenylbutyl) cyclopentane-1-carbonylamino-2, 3,4,5-tetrahydro-2-oxo-1H-1-benzazepine-1-acetic acid.

An injection solution was prepared having the following composition per 5 ml:

| | |
|---|---|
| (3S,2'R)-3-[1-(2'-Carboxy-4'-phenyl-butyl)-cyclopentane-1-carbonylamino]-2,3,4,5-tetrahydro-2-oxo-1H-1-benzazepine-1-acetic acid | 10 mg |
| Na$_2$HPO$_4$.7H$_2$O | 43.24 mg |
| NaH$_2$PO$_4$.2H$_2$O | 7.72 mg |
| NaCl | 30.0 mg |
| Purified water | 4948.0 mg |

The solids were dissolved in water and the solution was sterilized and aliquoted into ampoules in portions of in each case 5 ml.

The following examples are intended to explain the preparation of the compounds of the formula I in more detail.

EXAMPLE 3 tert-Butyl 3-{1-[2'-(ethoxycarbonyl)-4'-phenylbutyl] cyclopentane-1-carbonylamino}-2,3,4,5-tetrahydro-2-oxo-1H-1-benzazepine-1-acetate.

A) 123.4 g of potassium tert-butoxide were added in portions, at a temperature of 15° C., to a solution of 160.1 g of diethyl malonate in one litre of dimethylformamide. The reaction mixture was stirred for 30 minutes and a solution of 207.7 g of phenethyl bromide in 200 ml of dimethylformamide was then added dropwise at room temperature. The reaction mixture was subsequently heated at 60° C. for one hour and then allowed to cool down once again. The dimethylformamide was evaporated off under reduced pressure and the remaining residue was taken up in a mixture of methyl tert-butyl ether and water. The organic phase was separated, washed with water, dried over sodium sulfate and evaporated. The crude product, which remained as an oily residue, was purified by distillation under reduced pressure. 202.5 g of ethyl 2-ethoxycarbonyl-4-phenylbutanoate were obtained, b.p.$_{1.5}$=148°–153° C.

B) A solution of 6.17 g of potassium hydroxide in 76 ml of water was added, while cooling with ice, to a solution of 23.6 g of the diester product which was obtained above in 285 ml of ethanol. The reaction mixture was stirred at room temperature for several hours. The ethanol was then evaporated under reduced pressure, and the residue was taken up in a mixture of methyl tert-butyl ether and water. The organic phase was separated and discarded and the aqueous phase was acidified with dilute aqueous hydrochloric acid, while cooling with ice, and then extracted several times with methyl tert-butyl ether. The combined methyl tert-butyl ether phases were washed with water, dried over sodium sulfate and evaporated under reduced pressure. This resulted in 20.2 g of crude, oily ethyl 2-carboxy-4-phenylbutanoate, which was subjected to further processing without any further purification.

C) 11 ml of a 35% aqueous solution of formaldehyde and 9.23 ml of piperidine were added consecutively, while cooling with ice, to 20.2 g of the product which was obtained above. The reaction mixture was stirred at room temperature for several hours and then diluted with methyl tert-butyl ether, washed with aqueous potassium hydrogen sulfate solution and with water, dried over sodium sulfate and evaporated. The residue was dried under reduced pressure. 14.8 g of ethyl α-(2-phenylethyl)acrylate were obtained.

D) 25.2 ml of diisopropylamine were dissolved in 150 ml of absolute tetrahydrofuran, under a nitrogen atmosphere, and the solution was cooled down to –35° C. 100 ml of a 1.6-normal solution of butyl lithium in n-hexane were added dropwise to the solution. The reaction mixture was then stirred at 0° C. for 30 minutes, after which a solution of 8.1 ml of cyclopentanecarboxylic acid in 20 ml of absolute tetrahydrofuran was added dropwise. The reaction mixture was stirred at 0° C. for 2 hours. A solution of 16.8 g of the acrylic ester obtained under C) in 20 ml of absolute tetrahydrofuran was then added dropwise, after which the reaction mixture was left to stand at 0° C. for 2 hours and then at –15° C. for several hours. For the working-up, the reaction mixture was acidified with a 10% aqueous solution of hydrochloric acid and extracted with n-hexane. The organic phase was washed seven times with a half-saturated aqueous solution of sodium bicarbonate and once with water, dried over sodium sulfate and evaporated under reduced pressure. The crude product, which was obtained as a residue, was purified by flash chromatography on silica gel using n-hexane/ethyl acetate (8:2). 19.6 g of pure 1-[2'-ethoxycarbonyl)-4'-phenylbutyl]cyclopentane-1-carboxylic acid were obtained with a melting point of from 68° to 69° C.

E) 108.3 g of bromine were slowly added dropwise, while cooling with ice, to a solution of 100 g of α-tetralone in 820 ml of methanol. The reaction mixture was then stirred at room temperature for 30 minutes after which firstly 122.4 g of hydroxylamine hydrochloride and then 110 ml of water were added at room temperature. The mixture was stirred at room temperature for 3 days. A further 493 ml of water were then added, with a white precipitate separating out after one hour. The reaction mixture was stirred for a further 3 days and then cooled down to 5° C. The precipitate was filtered out with suction, washed with water and dried at 40° C. under reduced pressure. 136.7 g of 2-bromo-3,4-dihydronaphthalene-1(2H)-onoxime were obtained with a melting point of from 130° to 132° C.

F) 79.5 g of the oxime which was obtained above were added in portions to 452 g of polyphosphoric acid which had been heated to 80° C. and the reaction mixture was stirred at 80° C. for 18 hours. Subsequently, the reaction mixture was carefully diluted with 710 ml of water and stirred at room temperature for 2 hours. The resulting precipitate was filtered out with suction, washed with water, aqueous sodium bicarbonate solution, once again with water and finally with methyl tert-butyl ether and dried over potassium hydroxide at a temperature of 60° C. 66.6 g of 3-bromo-4,5-dihydro-1H-1-benzazepin-2(3H)-one were obtained with a melting point of from 168° to 170° C.

G) 80 g of the product which was obtained above were suspended in 140 ml of dimethylformamide. A solution of 72.6 g of potassium phthalimide in 205 ml of dimethylformamide was added to the suspension and the mixture was then stirred at 60° C. for 16 hours. For the working-up, it was cooled down to room temperature and 800 ml of water were slowly added dropwise; the mixture was then stirred for 2 hours while cooling with ice. The resulting crystal slurry was filtered out with suction, washed firstly with a water/dimethylformamide mixture and then with methyl tert-butyl ether, and subsequently dried at 60° C. for 2 days under reduced pressure. 73.3 g of 4,5-dihydro-3-phthalimido-1H-1-benzazepin-2 (3H) -one were obtained with a melting range of from 185° to 195° C.

H) A solution of 12.3 g of potassium tert-butoxide in 40 ml of dimethylformamide was added, while cooling with ice, to a suspension of 27 g of the product which was obtained above in 90 ml of dimethylformamide. After the mixture had been stirred for 30 minutes while cooling with ice, 20.7 g of tert-butyl bromoacetate were added dropwise over the space of one hour at from 0° to 50° C. The reaction mixture was stirred at 0° C. for one hour. It was then heated to 40° C. and 164 ml of water were added dropwise over the course of 3 hours and the mixture was then stirred at 30° C. for a further one hour. The aqueous solution was then decanted off from the precipitate which had formed and the remaining solid residue was crystallized from methyl tert-butyl ether. The crystals which had formed were filtered out with suction, washed with water and with methyl tert-butyl ether and dried at 60° C. at reduced pressure. 26.3 g of tert-butyl 2,3,4,5-tetrahydro-2-oxo-3-phthalimido-1H-1-benzazepine-1-acetate were obtained with a melting point of 194°–197° C.

I) 7 g of the ester which was obtained above were added, over a course of 5 minutes, to 13.8 ml of ethanolamine which had been heated to 80° C. After 5 minutes, a clear solution had formed, which solution was cooled at room temperature and diluted with 105 ml of toluene. The solution was extracted by shaking with 140 ml of a 5-aqueous solution of sodium chloride, after which the organic phase was separated, dried over sodium sulfate and concentrated by evaporation. The remaining residue was crystallized from methyl tert-butyl ether. 4.0 g of tert-butyl 3-amino-2,3,4,5-tetrahydro-2-oxo-1H-1-benzazepine-1-acetate were obtained with a melting point of from 117° to 118° C.

J) 2.9 g of the amine which was obtained above and 3.2 g of the acid which was obtained above under D) were dissolved in 100 ml of dichloromethane. 2.2 ml of N-methylmorpholine, 1.27 g of hydroxybenzotriazole and 3.81 g of N-ethyl-N-(3-dimethylaminopropyl) carbodiimide hydrochloride were added to the reaction mixture while cooling with ice. The reaction mixture was then stirred at room temperature for 1 hour. For the working-up, the reaction mixture was diluted with dichloromethane and washed consecutively with water, aqueous potassium hydrogen sulfate solution, water, aqueous sodium bicarbonate solution and once again with water. The organic phase was then dried over sodium sulfate and the solvent was evaporated under reduced pressure. The crude product which had been obtained in this way was purified by column chromatography on silica gel and at slightly elevated pressure (=flash chromatography) using n-hexane/ethyl acetate, with the proportion of ethyl acetate in the eluent being increased during the elution from 1:9 initially to 3:7. 5.4 g of the pure title compound were obtained as an oily product. IR spectrum (as a film): 3400 cm$^{-1}$, 1725 cm$^{-1}$, 1660 cm$^{-1}$

EXAMPLE 4

3-{1-[2'-(Ethoxycarbonyl)-4'-phenylbutyl]cyclopentane-1-carbonylamino}-2,3,4,5-tetrahydro-2-oxo-1H-1-benzazepine-1-acetic acid.

5 g of tert-butyl 3-{1-[2'-(ethoxycarbonyl)-4'-phenylbutyl]cyclopentane-1-carbonylamino}-2,3,4,5-tetrahydro-2-oxo-1H-1-benzazepine-1-acetate (preparation, see Example 3) were dissolved in 16 ml of trifluoroacetic acid. The solution was stirred at room temperature for 3 hours. For the working-up, the trifluoroacetic acid was evaporated under reduced pressure. The remaining residue was dissolved in dichloromethane and the solution was washed with water until neutral. The organic phase was subsequently dried over sodium sulfate and evaporated under reduced pressure. The remaining residue was stirred up several times with n-hexane and in each case evaporated once again to dryness. 3.4 g of the title compound were obtained as a solid foam having a melting range of from 81° to 104° C.

EXAMPLE 5 tert-Butyl (3S,2'R)-3-{1-[21-ethoxycarbonyl)-4'-phenylbutyl]cyclopentane-1-carbonylamino}-2,3,4,5-tetrahydro-2-oxo-1H-1-benzazepine-1-acetate.

A) 30.5 g of 1-[2'-(ethoxycarbonyl)-4'-phenylbutyl]-cyclopentane-1-carboxylic acid (preparation, see Example 3D) and 11.6 g of L-(−)-α-methylbenzylamine were dissolved, with heating, in ethanol. The reaction mixture was cooled for 12 hours in a refrigerator, after which the crystal slurry which had precipitated out was filtered with suction, dried and recrystallized several times (to rotation value constancy) from ethanol and subsequently dried under reduced pressure. 17.7 g of an α-methylbenzylammonium salt of the above acid were obtained with a melting point of 118° to 121° C. and with an optical rotation value $[\alpha]^{20}_D$=+5.6° (c=0.5 in methanol).

In order to liberate the acid, this salt was taken up in a water/dichloromethane mixture and the mixture was acidified with an aqueous solution of potassium hydrogen sulfate. The organic phase was separated and the aqueous phase was washed a further three times with dichloromethane. The combined organic extracts were washed with water, dried over sodium sulfate and evaporated under reduced pressure. The remaining residue was dried. 11.2 g of pure (2'R)-1-[2'-(ethoxycarbonyl-4'-phenylbutyl]cyclopentane-1-carboxylic acid were obtained with an optical rotation value $[\alpha]^{20}_D$=+7.4° (c=0.651 in methanol).

B) A solution of 12.65 g of L-(+)-tartaric acid in 54 ml of ethanol which had been heated to 650° C. was added to a solution, which had been heated to 65° C., of 24.5 g of the racemic tert-butyl 3-amino-2,3,4,5-tetrahydro-2-oxo-1H-1-benzazepine-1-acetate (preparation, see Example II). The reaction mixture was stirred at room temperature for one hour. A solution of 1.72 ml of benzaldehyde in 1.3 ml of ethanol was then added dropwise. The resulting suspension was boiled under reflux at 800° C. for 14 hours and then cooled down to room temperature. The resulting crystalline precipitate was filtered out with suction and taken up in 80 ml of ethanol; this solution was boiled under reflux for a further 8 hours. It was then cooled down to room temperature and the crystals were filtered out with suction and dried at 50° C. under reduced pressure. 23.6 g of tartaric acid salt were obtained with a melting point of from 195° to 196° C. and an optical rotation value $[\alpha]^{20}_D$ of −152° C. (c=0.5 in methanol). In order to liberate the base, 23.6 g of the tartaric acid salt in a mixture consisting of 250 ml of water and 108 ml of dichloromethane were cooled down to 0° C., while being stirred, and adjusted to pH 9.6 by adding aqueous ammonium solution. The organic phase was separated, and the aqueous phase was extracted with a further 30 ml of dichloromethane; the organic phases were combined, dried over sodium sulfate and concentrated under reduced pressure. The remaining residue was crystallized from methyl tert-butyl ether and dried under reduced pressure. 12.2 g of tert-butyl (3S)-3-amino-2,3,4,5-tetrahydro-2-oxo-1H-1-benzazepine-1-acetate were obtained with a melting point of from 113° to 115° C. and an optical rotation value $[\alpha]^{20}_D$ of −276.2° (c=0.5 in methanol).

C) 5.4 g of the acid which was prepared above under A) were dissolved in 60 ml of dry dichloromethane. 2.33 ml of triethylamine were added to the solution and the mixture was cooled down to −20° C. A solution of 1.31 ml of methanesulfonyl chloride in 5 ml of dry dichloromethane was then added slowly dropwise. After the mixture has been stirred for 15 minutes, a solution of 4.8 g of the amine which has been obtained above under B) and 2.33 ml of triethylamine in 60 ml of dichloromethane was added dropwise. The reaction mixture was then stirred at room temperature for 1 hour. For the working-up, the reaction mixture was added to water, and the organic phase was separated and washed with aqueous potassium hydrogen sulfate solution and then with water, dried over sodium sulfate, filtered and concentrated under reduced pressure. The remaining crude product was purified by flash chromatography on 500 g of silica gel using n-hexane/ethyl acetate (7:3). After drying under reduced pressure, 9.5 g of pure title compound were obtained as an oil and with an optical rotation value $[\alpha]^{20}_D$=115.2° (c=0.463 in methanol).

EXAMPLE 6

(3s,2'R)-3-{1-[21-(Ethoxycarbonyl)-4'-phenylbutyl]cyclopentane-1-carbonylamino}-2,3,4,5-tetrahydro-2-oxo-1H-1-benzazepine-1-acetic acid.

9.4 g of tert-butyl (3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetate (preparation, see Example 5) were dissolved in 15 ml of dichloromethane while cooling with ice. 31 ml of trifluoroacetic acid were added to the solution and the reaction mixture was kept at 40° C. in a refrigerator for approx. 12 hours. For the working-up, the dichloromethane and the trifluoroacetic acid were evaporated under reduced pressure. The resulting crude product was taken up in ethyl acetate and this solution was washed with water, dilute aqueous sodium bicarbonate solution and once again with water. The organic phase was separated, dried over sodium sulfate and evaporated under reduced pressure. The remaining residue was purified by flash chromatography on silica gel with firstly dichloromethane and then dichloromethane/methanol (95:5) being used as eluent. The resulting product was dried at 800° C. for 2 days under reduced pressure. 7.3 g of the pure title compound were obtained as a solid foam with a melting point of from 71° to 74° C. and with an optical rotation value $[\alpha]^{20}_D$=−131.0° (c=0.5 in methanol).

EXAMPLE 7 tert-Butyl 3-{1-[2'-(tert-butoxycarbonyl)-4'-phenylbutyl]cyclopentane-1-carbonylamino}-2,3,4,5-tetrahydro-2-oxo-1H-1-benzazepine-1-acetate.

A) 118 g of tert-butyl dimethylphosphonoacetate were dissolved, under a nitrogen atmosphere, in 875 ml of dry dimethylformamide. 58.9 g of potassium tert-butoxide were added to the solution while cooling with ice. The reaction mixture was subsequently heated at 60° C. for a short period and then allowed to cool down to room temperature. A solution of 104.9 g of phenethyl bromide in 110 ml of dimethylformamide was added dropwise to the reaction mixture. The reaction mixture was then heated at 60° C. for 2 hours. For the working-up, most of the dimethylformamide was evaporated under reduced pressure and the remaining residue was dissolved in methyl tert-butyl ether. The solution was acidified with aqueous potassium hydrogen sulfate solution. The organic phase was then separated, washed with water, dried over sodium sulfate and evaporated under reduced pressure. The resulting crude product was purified by flash chromatography on 3 kg of silica gel using dichloromethane/methyl tert-butyl ether (4:1) as the eluent. 105.1 g of pure tert-butyl 2-(dimethylphosphono)-4-phenyl-n-butyrate were obtained as an oily product.

B) 105.1 g of the product which was obtained above were dissolved, under a nitrogen atmosphere, in 705 ml of dry tetrahydrofuran. 28.4 g of paraformaldehyde were added to the solution. A solution of 32.5 g of potassium tert-butoxide in 100 ml of tetrahydrofuran was then added slowly dropwise. The reaction mixture was subsequently stirred for 1 hour. For the working-up, the reaction mixture was acidified with cold aqueous potassium hydrogen sulfate solution and diluted with methyl tert-butyl ether. The organic phase was then separated, washed with water, dried over sodium sulfate and concentrated under reduced pressure. The resulting crude product was purified by flash chromatography on 700 g of silica gel using n-hexane/ethyl acetate (9:1). 47.0 g of tert-butyl α-(phenethyl)acrylate were obtained as a colorless oil.

C) 200 ml of a 1.6-molar solution of butyl lithium in n-hexane were added dropwise to a solution, which had been cooled down to −50° C., of 50.2 ml of diisopropyl-amine in 450 ml of absolute tetrahydrofuran and the reaction mixture was kept at 0° C. for a further 30 minutes. A solution of 16.2 ml of cyclopentane carboxylic acid in 40 ml of absolute tetrahydrofuran was then added dropwise at this temperature. The reaction mixture was stirred at 00° C. for a further 2 hours. A solution of 38 g of the product which was obtained above under B) in 50 ml of absolute tetrahydrofuran was then added slowly to the mixture. The reaction mixture was stirred at 0° C. for a further 2 hours and then left to stand at −150° C. for several more hours. For the working-up, the reaction mixture was acidified, while cooling with ice, with saturated aqueous potassium hydrogen sulfate solution and extracted three times with n-hexane. The combined organic phases were washed seven times with a half-saturated aqueous solution of sodium bicarbonate and subsequently with water, and then dried over sodium sulfate and evaporated under reduced pressure. The resulting oily crude product was crystallized from ice-old n-hexane. 41.9 g of pure crystalline 1-[2'-tert-butoxycarbonyl)-4'-phenylbutyl]cyclopentane-1-carboxylic acid were obtained with a melting point of from 75° to 77° C.

D) 3.3 g of the product which was obtained above, 2.7 g of tert-butyl 3-amino-2,3,4,5-tetrahydro-2-oxo-1H-1-benzazepine-1-acetate (preparation, see Example 3I)), 1.53 ml of N-methylmorpholine and 1.18 g of hydroxybenzotriazole were dissolved, under a nitrogen atmosphere, in 93 ml of absolute dichloromethane. 3.52 g of N-ethyl-N'-(3-dimethylaminopropyl)carbodiimide hydrochloride were added to this solution while cooling with ice. The reaction mixture was then stirred for 2 hours while cooling with ice. For the working-up, the reaction mixture was washed consecutively with water, aqueous potassium hydrogen sulfate solution, water, aqueous sodium bicarbonate solution and once again with water. The organic phase was dried over sodium sulfate and concentrated under reduced pressure. The remaining crude product was purified by flash chromatography on 200 g of silica gel using n-hexane/ethyl acetate (7:3) as the eluent and crystallized from methyl tert-butyl ether. 4.2 g of the pure title compound were obtained with a melting point of from 110° to 114° C.

EXAMPLE 8

3-[1-(2'-Carboxy-4'-phenylbutyl)cyclopentane-1-carbonylamino]-2,3,4,5-tetrahydro-2-oxo-1H-1-benzazepine-1-acetic acid.

4.1 g of tert-butyl 3-{1-[2'-(tert-butoxycarbonyl)-4'-phenylbutyl]cyclopentane-1-carbonylamino}-2,3,4,5-tetrahydro-2-oxo-1H-1-benzazepine-1-acetate (preparation, see Example 7) were dissolved in 13 ml of trifluoroacetic acid at a temperature of 4° C. and while excluding moisture. The resulting solution was stirred at this temperature for a further 3 hours. For the working-up, the reaction mixture was concentrated under reduced pressure. In order to remove trifluoroacetic acid completely, dichloromethane was added several times to the residue and evaporated off once again. The resulting residue was then dissolved in dichloromethane, and the solution was washed with water, dried over sodium sulfate and concentrated under reduced pressure. The crude product remaining as a residue was crystallized from dichloromethane. 2.7 g of the pure title compound were obtained with a melting point of from 178° to 183° C.

EXAMPLE 9

Benzyl 3-{1-[2'-(tert-butoxycarbonyl)-4'-phenylbutyl]cyclopentane-1-carbonylamino}-2,3,4,5-tetrahydro-2-oxo-1H-1-benzazepine-1-acetate.

A) 10.5 g of tert-butyl 3-amino-2,3,4,5-tetrahydro-2-oxo-1H-1-benzazepine-1-acetate (preparation, see Example 3I), 8.25 g of p-toluenesulfonic acid hydrate and 20.1 ml of benzyl alcohol were added to 174 ml of toluene. The reaction mixture was boiled for 4 hours on a water separator, during which period a precipitate which had originally separated out went slowly in solution. After that, the toluene was swept off under reduced pressure and the remaining residue was stirred with methyl tert-butyl ether and then filtered off. The solid residue which was obtained in this way was dissolved in dichloromethane and the solution was rendered alkaline by adding aqueous sodium carbonate solution while cooling with ice. After that, the dichloromethane phase was separated, washed with water, dried over sodium sulfate and evaporated. The resulting crude product was recrystallized, for purification, from methyl tert-butyl ether. 8.2 g of benzyl 3-amino-2,3,4,5-tetrahydro-2-oxo-1H-1-benzazepine-1-acetate were obtained with a melting point of from 105° to 107° C.

B) 12.8 g of the product which was obtained above were reacted with 13.7 g of 1-[2'-tert-butoxycarbonyl)-4'-phenylbutyl]cyclopentane-1-carboxylic acid (preparation, see Example 5C)) using the method described in Example 5C) . The reaction mixture was worked up as described in Example 5C). 19.3 g of the title compound were obtained with a melting point of from 118° to 123° C.

EXAMPLE 10

Benzyl 3-[1-(2'-carboxy-4'-phenylbutyl) cyclopentane-1-carbonylamino]-2,3,4,5-tetrahydro-2-oxo-1H-1-benzazepine-1-acetate.

15 g of benzyl 3-{1-(21-tert-butoxycarbonyl)-4'-phenylbutyl]cyclopentane-1-carbonylamino}-2,3,4,5-tetrahydro-2-oxo-1H-1-benzazepine-1-acetate (preparation, see Example 9) were reacted with 56 ml of trifluoroacetic acid using the method described in Example 8. The reaction mixture was worked up as described in Example 8, and the resulting crude product was crystallized from methyl tert-butyl ether. 13.1 g of the title compound were obtained with a melting point of from 86° to 90° C.

EXAMPLE 11

Benzyl 3-{1-[2'-(tert-butylcarbonyloxymethoxycarbonyl)-4'-phenylbutyl]cyclopentane-1-carbonylamino}-2,3,4,5-tetrahydro-2-oxo-1H-1-benzazepine-1-acetate.

2 g of benzyl 3-[1-(2'-carboxy-4'-phenylbutyl)-cyclopentane-1-carbonylamino]-2,3,4,5-tetrahydro-2-oxo-1H-1-benzazepine-1-acetate (preparation, see Example 10) were dissolved in 20 ml of dry dichloromethane while excluding moisture. 0.46 ml of triethylamine and 0.1 g of dimethylaminopyridine were added to the solution. A solution of 0.5 g of chloromethyl pivalate in 3 ml of dry dichloromethane were then added dropwise while cooling with ice. The reaction mixture was subsequently stirred at room temperature for 2 days. For the working-up, the reaction mixture was added to water and the organic phase was separated off, washed with aqueous sodium bicarbonate solution and then with water, dried over sodium sulfate and concentrated under reduced pressure. The crude product which remained as a residue was purified by flash chromatography on 150 g of silica gel with an n-hexane/ethyl acetate mixture having a composition of initially 7:3 and then 1:1 being employed as the eluent. 1.1 g of pure benzyl 3-{1-[2'-(pivaloyloxymethoxycarbonyl)-4 1-phenylbutyl] cyclopentane-1-carbonylamino}-2,3,4,5-tetrahydro-2-oxo-1H-1-benzazepine-1-acetate were obtained as a solid foam with a melting range of 71°-78° C.

EXAMPLE 12

3-{1-[2'-(Pivaloyloxymethoxycarbonyl)-4'-phenylbutyl] cyclopentane-1-carbonylamino}-2,3,4,5-tetrahydro-2-oxo-1H-1-benzazepine-1-acetic acid.

1.0 g of benzyl 3-{1-[21-(pivaloyloxymethoxycarbonyl)-4'-phenylbutyl]cyclopentane-1-carbonylamino}-2,3,4,5-tetrahydro-2-oxo-1H-1-benzazepine-1-acetate (preparation, see Example 11) was dissolved in 100 ml of ethanol. 0.5 g of palladium/carbon catalyst (5% strength) was added to the solution. The mixture was then hydrogenated for 3 hours using a hydrogen pressure of 5 bar. For the working-up, the catalyst was filtered out and the filtered solution was evaporated. The resulting residue was dried at 80° C. under reduced pressure. 0.7 g of the title compound was obtained glassy product.

IR spectrum (as a KBr pressed disc): 3410 cm$^{-1}$, 1750 cm$^{-1}$, 1660 cm$^{-1}$.

The compounds of the formula I which are listed in Table 1 below can also be prepared using the methods which are described in the above examples.

TABLE 1

| Ex. No. | R$^1$ | R$^2$ | R$^3$ | Steric arrangement in position C-side | Steric arrangement in position C-ring | Notes M.p. = melting range in °C. IR spectrum in KBr Bands in cm$^{-1}$ |
|---|---|---|---|---|---|---|
| 13 | phe-CH$_2$—CH$_2$— | H | H | rac | rac | acid, foam, m.p.: 79–95 |
| 14 | phe-CH$_2$—CH$_2$— | H | H | rac | S-c | acid, foam, m.p.: from 113 |
| 15 | nap-CH$_2$—CH$_2$— | H | H | rac | rac | acid, oil IR: 2949, 1726, 1632, 1195 |
| 16 | phe-CH$_2$— | H | H | rac | rac | acid, m.p.: 216–217 |
| 17 | phe-CH$_2$— | H | H | rac | S-c | acid, m.p.: 116–117 |
| 18 | 4-CH$_3$-phe-CH$_2$— | H | H | rac | rac | acid, m.p.: 223–225 |
| 19 | phe-CH$_2$—CH$_2$— | (CH$_3$)$_3$C | H | rac | rac | acid, m.p.: 195–196 |
| 20 | phe-CH$_2$—CH$_2$— | ind | H | rac | rac | acid, m.p.: 146–149 |
| 21 | phe-CH$_2$—CH$_2$— | diox | H | rac | rac | acid, oil IR; 3410, 2950, 1735, 1660 |
| 22 | phe-CH$_2$—CH$_2$— | phe | H | rac | rac | acid, m.p.: 108–111 |
| 23 | phe-CH$_2$—CH$_2$— | H | H | R-c | S-c | Na, m.p.: >270 |
| 24 | nap-CH$_2$— | H | H | rac | rac | acid, m.p.: 165–170 |
| 25 | phe-CH$_2$—CH$_2$— | H | H | R-c | S-c | acid, foam IR: 3402, 2949, 1723, 1633 |
| 26 | nap-CH$_2$—CH$_2$— | C$_2$H$_5$ | H | R-c | S-c | | phe = phenyl, nap = α-naphthyl, ind = 5-indanyl, diox = (2,2-dimethyl-1,3-dioxolan-4-yl)methyl, C-side = asymmetric center in the side chain, C-ring = asymmetric center in the ring skeleton, rac = racemic, R-c = R-configured, S-c = S-configured, foam = foam resin, oil = oily, acid = free acid, Na = disodium salt

What is claimed is:

1. A method of promoting gastrointestinal blood circulation in a mammal, said method comprising administering to said mammal an effective gastrointestinal blood circulation promoting amount of a compound corresponding to the formula I

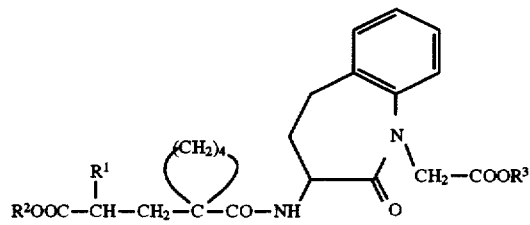

wherein

R$^1$ represents a phenyl-lower alkyl group which can optionally be substituted in the phenyl ring by lower alkyl, lower alkoxy or halogen, or represents a naphthyl-lower alkyl group, R$^2$ denotes hydrogen or a biolabile ester-forming group, and R$^3$ denotes hydrogen or a biolabile ester-forming group, or a physiologically acceptable salt of an acid of formula I.

2. A method according to claim 1, wherein at least one of R$^2$ and R$^3$ represents a biolabile ester-forming group.

3. A method according to claim 1, wherein the biolabile ester-forming group represents:

a lower alkyl group, a phenyl or phenyl-lower alkyl group which is optionally substituted in the phenyl ring by lower alkyl or by a lower alkylene chain which is bonded to two adjacent carbon atoms, a dioxolanyl methyl group which is optionally substituted in the dioxolane ring by lower alkyl, or a $C_2$–$C_6$-alkanoyloxymethyl group which is optionally substituted on the oxymethyl group by lower alkyl.

4. A method according to claim 3, wherein the biolabile ester forming group is selected from the group consisting of phenyl, benzyl, indanyl and (2,2-dimethyl-1,3-dioxolan-4-yl)methyl.

5. A method according to claim 1, wherein $R^2$ denotes a biolabile ester-forming group and $R^3$ is hydrogen.

6. A method according to claim 5, wherein said compound is (3S,2'R)-3-{1-[2'-(ethoxycarbonyl)-4'-phenylbutyl]cyclopentane-1-carbonylamino}-2,3,4,5-tetra-hydro-2-oxo-1H-1-benzazepine-1-acetic acid, or a physiologically acceptable salt thereof.

* * * * *